United States Patent [19]

Toback et al.

[11] Patent Number: 5,135,856
[45] Date of Patent: Aug. 4, 1992

[54] PRODUCTION OF AUTOCRINE GROWTH FACTORS

[75] Inventors: F. Gary Toback; Margaret M. Walsh-Reitz, both of Chicago, Ill.; Stephen L. Gluck, St. Louis, Mo.

[73] Assignee: ARCH Development Corp., Chicago, Ill.

[21] Appl. No.: 66,059

[22] Filed: Jun. 24, 1987

[51] Int. Cl.$^5$ .................. C12P 21/00; C12N 5/06; C12N 5/02
[52] U.S. Cl. .................. 435/70.1; 435/240.2; 435/240.3; 435/240.31; 530/399
[58] Field of Search .................. 435/68, 240.1, 240.2, 435/240.54, 240.3, 240.31, 70.1; 530/399

[56] References Cited
PUBLICATIONS

Walsh-Reitz et al., 1986 Proc. Natl. Acad. Sci. USA 83, 4764–4768.
Holley et al., 1980 Proc. Natl. Acad. Sci. USA 77, 5989–5992.
Moolenaar et al., 1981 Cell 23, 789–798.
Sporn et al., 1985 Nature 313, 745–747.
Mordan et al., 1984 Am. J. Physiol. 246, C351–C354.
Walsh-Reitz et al., 1984 Am. J. Physiol. 247, C321–C326.
Toback et al., 1984 Am. J. Physiol. 247, C14–C19.

*Primary Examiner*—Jacqueline Stone
*Assistant Examiner*—Christopher S. F. Low
*Attorney, Agent, or Firm*—Arnold, White & Durkee

[57] ABSTRACT

A method of producing autocrine growth factors from kidney epithelial cells by lowering the extracellular sodium concentration. The invention also concerns new growth factors, a method of producing the new growth factors, and the medium used to produce these new growth factors.

3 Claims, 5 Drawing Sheets

PRODUCTION OF AUTOCRINE GROWTH FACTORS

The government may own certain rights in the present invention pursuant to NIH grant number DK39689.

FIELD OF THE INVENTION

The present invention relates to a method of producing autocrine growth factors by lowering the extracellular sodium concentration of kidney epithelial cells. The invention also concerns new growth factors, a method of producing the new growth factors and the medium used to produce the new growth factors.

BACKGROUND OF THE INVENTION

Cell multiplication can be enhanced in kidney epithelial cells through the stimulation and release of endogenous growth factors. Growth factors comprise any substance, either genetic or extrinsic, which affect growth. Blakiston's Gould Medical Dictionary, 4th Edition, McGraw Hill Publishing Company, Copyrighted 1956, 1972 and 1979. There is interest in methods that increase cell replication through endogenous growth factors that include: one, the ability to recruit unstimulated cells to replicate; two, the enhancement of mitogenesis; and three, the regulation of ion and nutrient transport in adjacent and nonadjacent epithelial cells.

The self-stimulation of cell proliferation by endogenous growth factors was first demonstrated by Todaro and DeLarco in cultures of virus-transformed fibroblasts ("Growth factors produced by sarcoma virus-transformed cells" *Cancer Res:* 38: 4147–4154, 1978.). It was proposed that proliferation of these cells was under autocrine control since they secreted growth-promoting polypeptides. Further studies revealed that endogenous growth-stimulating proteins could be isolated from nontransformed fibroblasts and normal tissues. Thus, proliferation of fibroblasts could be mediated by the interaction of growth-stimulating and inhibiting polypeptides.

Later studies showed that the stimulation of renal epithelial cell growth could be induced by lowering the potassium concentration in extracellular fluid. (see "Growth of kidney epithelial cells in culture: evidence for autocrine control"; Lawrence J. Mordan and F. Gary Toback, *Am. J. Physiol.* 246: C351–C354, 1984). Specifically, the stimulation of renal epithelial cell growth, associated with the appearance of mitogenic factors in the extracellular fluid, was induced by lowering the extracellular potassium concentration. It was found that these renal epithelial cells transduce the information inherent in a reduction of the medium potassium concentration into endogenous growth-stimulating factors, which appeared in the medium.

Specifically, the study "Growth of kidney epithelial cells in culture: evidence for autocrine control" involved exposing epithelial cells from the African green monkey kidney (BSC-1 line) to three different types of media: one, low potassium conditioned medium; two, control conditioned medium; and three, unconditioned fresh medium. The study revealed that the epithelial cells that were exposed to fresh low potassium medium (3.2 millimolar potassium) grew to a higher density than cells in control medium (5.4 millimolar potassium). Low potassium medium, which had been conditioned by cultures of confluent quiescent BSC-1 cells for at least 1 hour, was collected and adjusted to 5.4 millimolar potassium by adding potassium chloride. The adjusted conditioned low potassium medium was then applied to fresh cultures to assess its effect on cell growth.

The results showed that sparse cultures of BSC-1 cells exposed to this medium grew to a higher density than cultures exposed to conditioned medium prepared at the control potassium concentration. Growth-stimulating activity in low potassium conditioned medium was optimal at a potassium concentration of 3.2 millimolar, which was the same potassium concentration required for optimal growth with unconditioned fresh medium. One hour of exposure of BSC-1 cells to low potassium conditioned medium was required to increase the growth-stimulating activity of this medium above that in control conditioned medium. This amount of growth-stimulating activity was constant for up to 12 hours. Control medium conditioned for 12 hours enhanced growth compared with media conditioned for less time. Both control and low potassium conditioned media stimulated growth to a greater extent after 15 to 45 minutes than did unconditioned fresh medium.

Thus, this study indicated that growth-stimulating activity in low-potassium conditioned medium was optimal when the potassium concentration during the one to six hours of conditioning was 3.2 millimolar. Control conditioned medium also contained growth-stimulating activity compared with unconditioned medium. Hence, the results suggested that BSC-1 cells exposed to low-potassium medium produce a larger quantity of growth-stimulating factors and/or different ones than do control cells.

Prior to the present invention, it was known that renal epithelial cell growth could be stimulated by lowering the concentration of extracellular potassium. However, alternatives to that state of the art are important, especially if lowering the extracellular potassium concentration is not desired. The present invention provides an alternative to lowering the concentration of extracellular potassium to produce autocrine growth factors.

SUMMARY OF THE INVENTION

Accordingly, an object of the present invention is to provide a process for the proliferation of kidney epithelial cells. Specifically, it is an object of the present invention to provide an improved process for the proliferation of kidney cells that involves a reduction in extracellular sodium concentration and the rapid release of autocrine growth factors by the cells.

It is also an object of this invention to provide an improved process for the proliferation of cells wherein the growth factors are identifiable.

It is a further object of this invention to provide an improved process which substantially reduces the time required to obtain the release of growth-stimulating activity, and thus expedites the epithelial cell multiplication.

Sodium influx is an important early signal during the onset of mitogenesis in many types of cells. From this observation, one would predict that a decrease in extracellular sodium concentration might retard cell proliferation. However, the present invention unexpectedly provides a method of producing autocrine growth factors by lowering the extracellular sodium concentration.

DETAILED DESCRIPTION OF THE PREFERRED EMBODIMENTS

Figure 1:
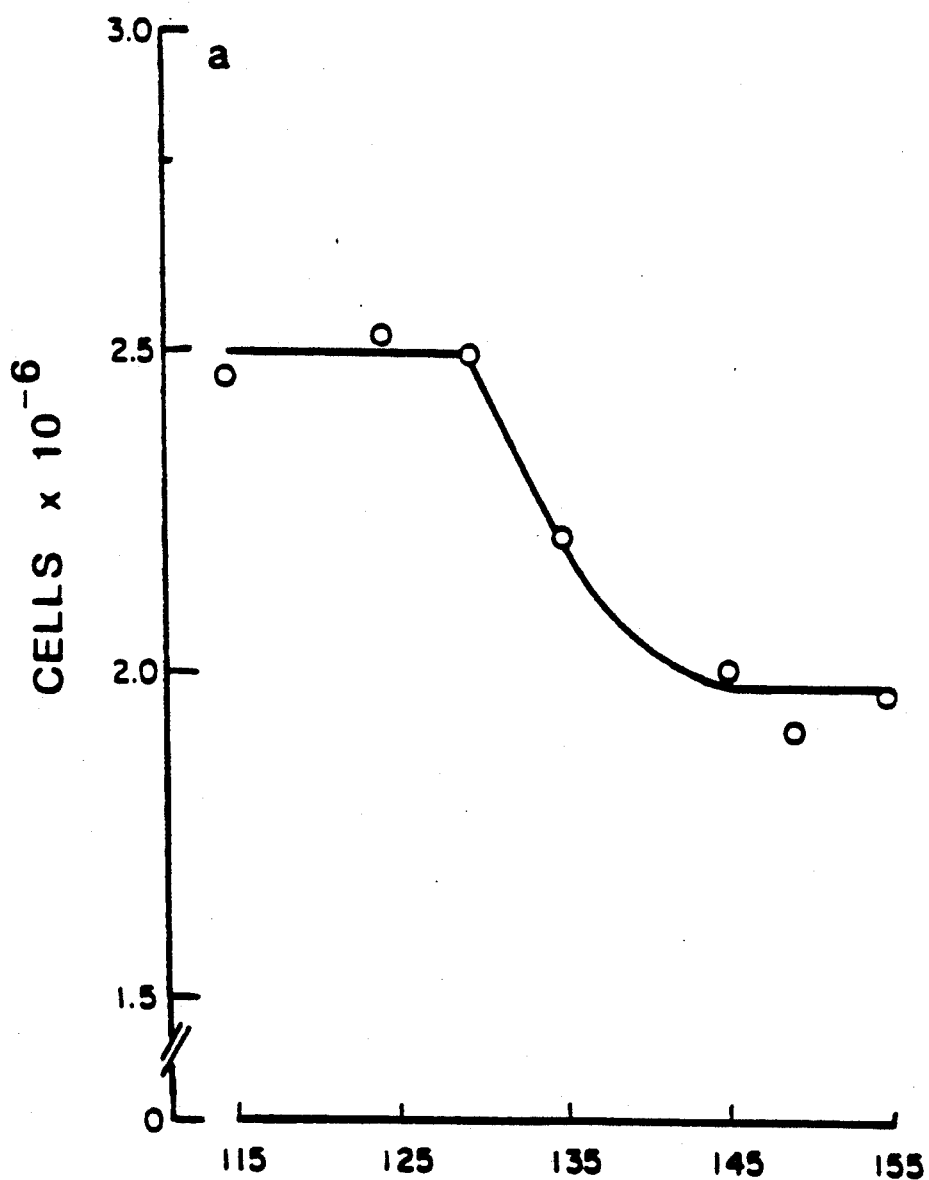

As noted above, prior to the present invention the growth of renal epithelial cells (BSC-1 line) was accelerated in media containing a reduced concentration of potassium. However, the stimulation of renal epithelial cells in potassium-deficient medium required from one to six hours of conditioning with the medium. In contrast, the present invention drastically accelerates the growth rate of epithelial cells in medium with reduced concentrations of sodium which requires as little as five minutes of exposure to the medium.

Moreover, the present invention identifies the growth factors by their molecular weights. Initial experiments proved that a decrease in the sodium concentration of the medium from the control value of 155 millimolar (control) to 115 millimolar (low sodium) stimulated growth up to 30% as assessed by counting the number of cells per 60-millimeter culture dish after 4 days. In subsequent experiments, the sodium concentration of low sodium media was set at 130 millimolar and optimal growth stimulation occurred after five minutes of exposure to the medium.

The determination of the time required for the low sodium signal to exert its mitogenic effect was achieved by exposing confluent cultures to low sodium medium for different periods of time. At the end of a defined period, the growth signal was terminated by adding a sodium chloride solution to the culture medium to restore its sodium concentration to the control value. Only five minutes of exposure to low sodium media was required for maximal growth stimulation under these conditions. This observation suggested that reduction of the sodium concentration resulted in the release and/or synthesis of growth-promoting factors by the cells that appeared in the medium. This hypothesis was tested by exposing cells to low sodium media containing only 0.01% serum for short intervals up to 5 min and then removing these conditioned media from the dish. Sodium was added to conditioned media to give 155 millimolar, and the media were filtered and then added to fresh cultures of BSC-1 cells. Conditioned media from cells exposed to the low sodium signal for 3–5 minutes stimulated cell multiplication by 40% compared to conditioned media from cells exposed to a sodium concentration of 155 millimolar. The growth-promoting effect of the conditioned media was not affected by the presence or absence of choline chloride during conditioning.

These observations indicate that low-sodium medium can induce these renal cells to release growth-stimulating factors into the extracellular fluid. Exposure of cells to media containing a sodium concentration of 155 millimolar for five minutes did not impart growth-stimulating activity to these conditioned media.

The present invention is illustrated by the following example. Epithelial cells from the African green monkey kidney line BSC-1 and a strain of mouse fibroblasts, clone 1 D, were grown in 60-millimeter plastic dishes (Nunc) in Dulbecco-Vogt modified Eagle's medium (DMEM) (containing 25 millimolar glucose and 155 millimolar sodium) with 1.6 micromolar biotin, and 1% calf serum at 38° C. in a $CO_2$ incubator. Media containing specified sodium concentrations were prepared by adding NaCl to DMEM that contained 100 millimolar sodium. BSC-1 cells became confluent at $10^6$ cells per 60-millimeter dish and fibroblasts were confluent at $4 \times 10^6$ cells per dish.

Cells were then grown to a density of $10^6$ cells per dish in DMEM containing 1.6 micromolar biotin and 1% calf serum. At time 0, this medium was aspirated, and the cells were exposed to medium containing specified amounts of sodium, 1.6 micromolar biotin, and 0.5% serum. On day 4, the cell monolayer was rinsed, detached from the dish with crystalline trypsin, dispersed, and the number of cells was counted with a hemocytometer.

The medium on confluent cultures of epithelial or fibroblastic cells was aspirated and then replaced with fresh medium (5 milliliters) containing a sodium concentration of 155 millimolar (control) or 130 millimolar (low sodium), 1.6 micromolar biotin, and 0.01% serum. Cells were allowed to condition this medium for specified times. The conditioned media were collected and sterilized by passage through a 0.22-um Millex-GV filter (Millipore) that also removed any suspended cells and cell debris. The conditioned media also underwent a purification process (see below). The sodium concentration of low sodium conditioned medium was adjusted to 155 millimolar by adding a solution of NaCl. The serum concentration of each conditioned medium was increased to 0.5% by adding serum. Each conditioned medium was then assessed for its effect on cell growth. The medium on a confluent culture was replaced with 5 milliliters of conditioned medium, and the number of cells was counted 4 days later.

The amount of growth-promoting activity in control and low-sodium conditioned media was assessed by serial dilution. The sodium concentration of low sodium conditioned media was raised to 155 millimolar by adding NaCl, and the serum concentration was adjusted to 0.5%. Dilution of each conditioned medium was carried out with fresh unconditioned medium containing 155 millimolar sodium, 1.6 micromolar biotin, and 0.5% serum. Growth-stimulating activity of each medium was measured in cultures of BSC-1 cells as described above.

Cultures of confluent BSC-1 cells were exposed to low sodium medium containing 0.01% serum for 4–5 minutes to prepare conditioned media. The pooled medium from 60 dishes (300 milliliters) was passed through a 0.22-um filter to remove any cells or debris. The sodium concentration of the conditioned media was adjusted to 155 millimolar by adding sodium chloride, and the conditioned medium was then subjected to ultrafiltration through a YM 10 membrane (Amicon) to eliminate molecules with an apparent molecular weight of more than 10,000.

The filtrate was placed in Spectra/por 6 dialysis tubing that retained molecules with an apparent molecular weight of greater than 3500, and it was dialyzed at 4° C. against 10 millimolar sodium phosphate buffer (pH 7.2) ($NaP_1$). The retained material (molecular weight, greater than 3500 and less than 10,000) was lyophilized, reconstituted in 4 milliliters of $NaP_i$ buffer, and then applied to a Bio-Gel P-10 column (100–200 mesh, $1.5 \times 90$ cm) equilibrated with 150 millimolar $NaP_i$. The column was eluted at 4° C. with the same buffer at a flow rate of 10 milliliters/hr, and 2-milliliter fractions were collected.

Each fraction was assayed for growth-stimulating activity by adding a 100-ul aliquot to a test plate containing $10^6$ BSC-1 cells per dish in DMEM with 0.5% serum in triplicate. Four days later the cells were counted. Fractions containing growth-promoting activity were pooled, dialyzed against 10 millimolar NaP$_i$ buffer, loaded onto a Mono Q column for HPLC, and eluted for 30 minutes with a linear gradient of choline chloride (0.1-0.4 molar) in 10 millimolar NaP$_i$ buffer.

The capacity of each fraction (1 milliliter) to stimulate growth was assessed by adding a 50 microliter aliquot to the culture medium of $10^6$ BSC-1 cells in triplicate, and the number of cells per culture was counted after 4 days. The fractions of interest were pooled, dialyzed as described above, lyophilized, dissolved in sample buffer, and subjected to electrophoresis on a NaDodSO$_4$/polyacrylamide gel containing 15% acrylamide and 6 molar urea. Proteins on the gel were displayed by silver staining.

The results are evidenced by FIGS. 1-5.

FIG. 1 shows the effect of sodium concentration in the culture medium on the growth of confluent BSC-1 cells. Cells were grown to a density of $10^6$ cells per dish in medium containing 1.6 micromolar biotin and 1% calf serum. At time 0, this medium was aspirated, and the cells were exposed to medium containing the concentration of sodium specified on the abscissa, 1.6 micromolar biotin, and 0.5% calf serum. Cells were counted in a hemocytometer four days later. When the sodium concentration of the medium was reduced, sufficient choline chloride was added so that the sum of sodium and choline concentrations was 155 millimolar. Cell multiplication in low sodium medium was increased compared with the control (155 millimolar) at medium sodium concentrations of 130-115 millimolar (P less than 0.001).

Figure 2:
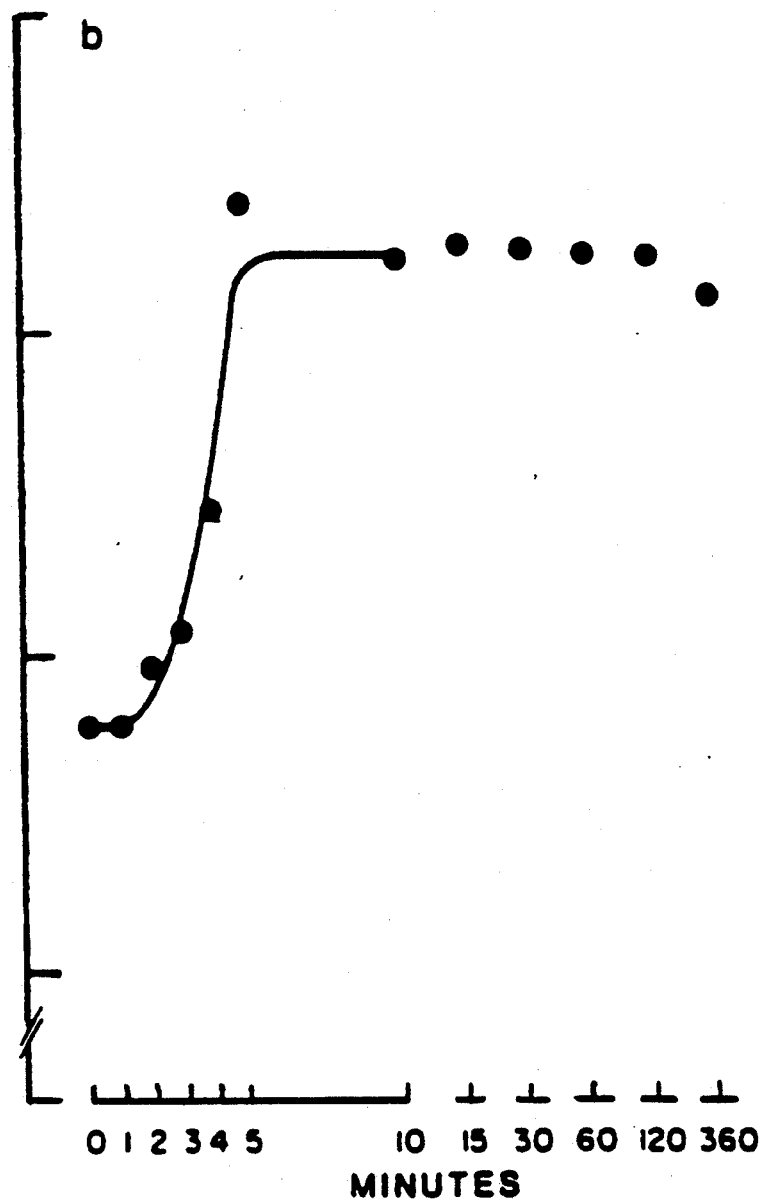

FIG. 2 shows growth of BSC-1 cells after exposure to low sodium medium for different amounts of time. At time 0, cells were exposed to low sodium medium (130 millimolar), and at the times specified on the abscissa sufficient sodium choloride was added to raise the sodium concentration to 155 millimolar. Cell counts were performed on day four. Exposure to low sodium medium for three (P less than 0.05) to four minutes (P less than 0.001) was sufficient to exert a growth-stimulating effect.

Figure 3:
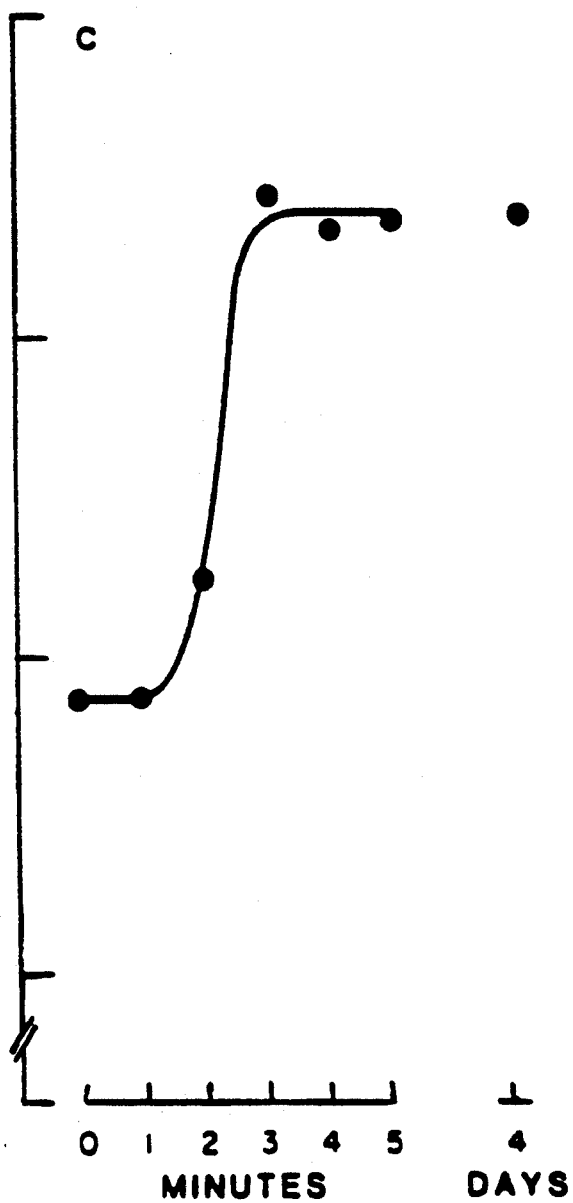

FIG. 3 shows the appearance of growth-promoting activity in low sodium medium. At time 0, low sodium medium with 0.01% serum was added to confluent cells. At the times specified on the abscissa, the conditioned medium on the dish (5 milliliters) was collected. The sodium concentration of low sodium conditioned medium was adjusted to 155 millimolar by adding sodium chloride. The conditioned medium was filtered and its serum concentration was raised to 0.5%. Medium on a fresh culture of BSC-1 cells was aspirated and replaced by this low-sodium conditioned medium (5 milliliters). The number of cells per dish was determined four days later. Growth-promoting activity was detected in low sodium conditioned medium after three minutes (P less than 0.001). Each value represents the mean of three to five experiments performed in triplicate; standard error was less then three percent of the mean.

Figure 4:
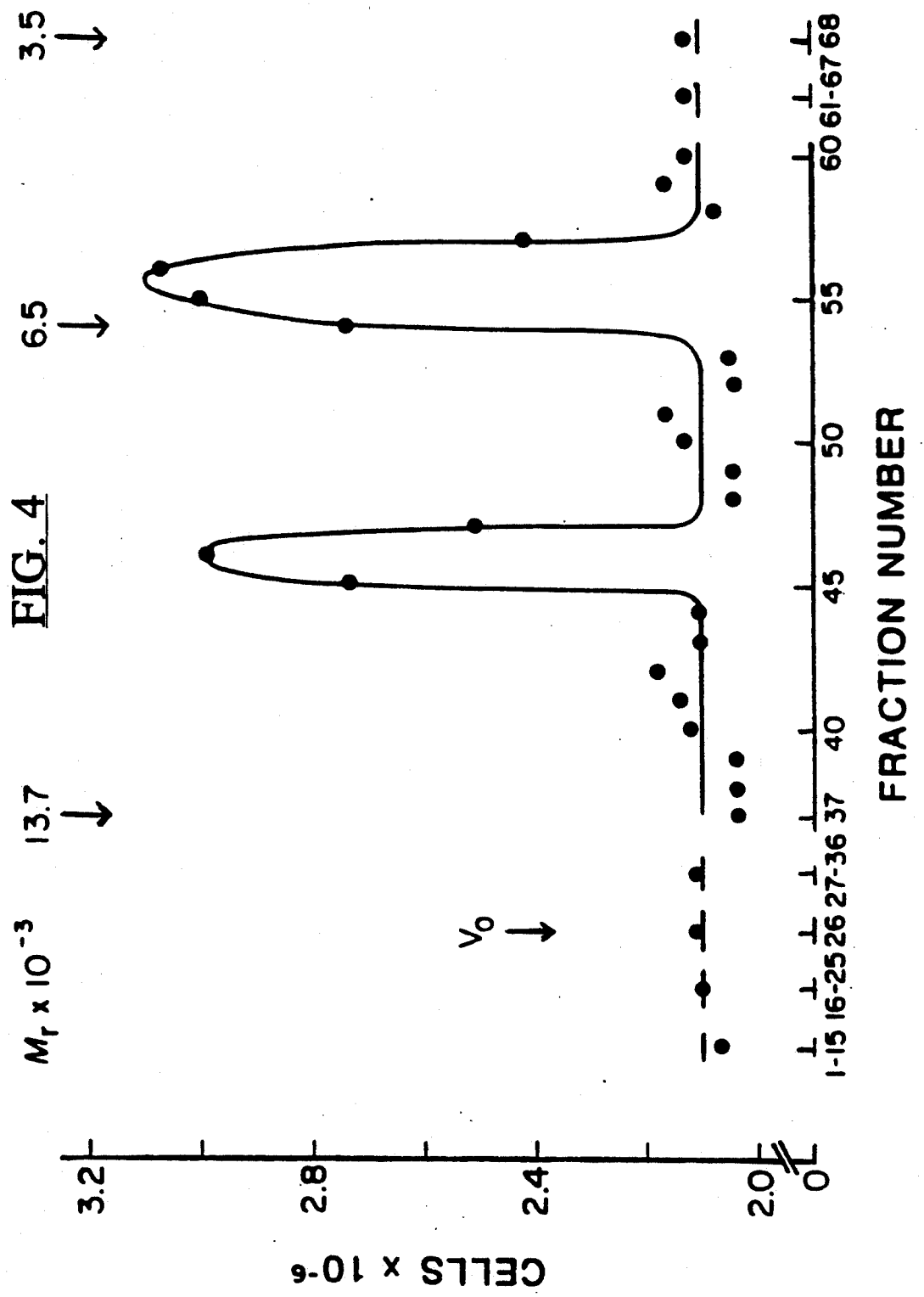

FIG. 4 shows gel-filtration chromotogram of partially purified growth-promoting activity obtained from low sodium conditioned media. Cultures of BSC-1 cells (60 dishes) were exposed to low sodium medium for four to five minutes to prepare 300 milliliters of control medium, which was then ultrafiltered, dialyzed, and concentrated as described. The active material, with an apparent molecular weight of more than 3500 and less than 10,000, was loaded onto a Bio-Gel P-10 column and eluted with ten millimolar of sodium phosphate buffer. An aliquot of each fraction was assayed for growth-stimulating activity on a culture of BCS-1 cells. Each value is the mean for three cultures; standard error was less than three percent of the mean. The column was calibrated by using protein samples of known molecular weight, as indicated by the vertical arrows (from left to right: RNase A, aprotinin, and ACTH; void volume, Vo, by ovalbumin). The apparent molecular weight of the growth stimulating activities was about 6200 and about 9000.

Figure 5:
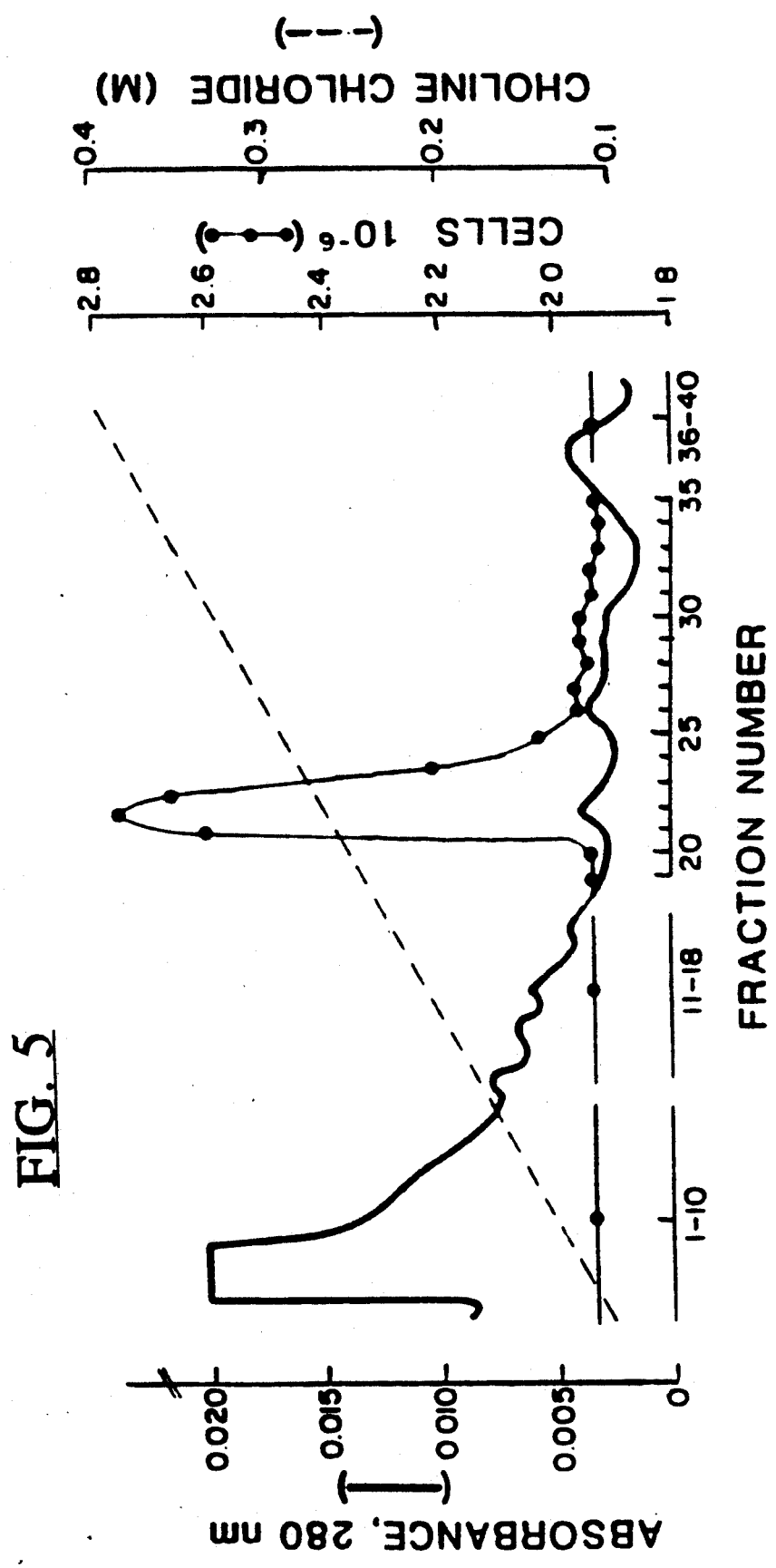

FIG. 5 shows high-performance anion exchange liquid chromotography of growth-promoting activity produced by BSC-1 cells exposed to low sodium medium. Fractions 54-56 from the Bio-Gel P-10 column shown in FIG. 4 were pooled and loaded onto a Mono Q column for HPLC and eluted with a linear gradient of choline chloride (0.1-0.4 molar) in 10 millimolar sodium-phosphate buffer. The thick line shows the absorbance tracing of the eluted fractions. Growth-stimulating activity in each fraction (one milliliter) was assayed in triplicate. The number of cells per culture is depicted on the graph as solid circles. Only fractions 21-23 contained growth-promoting activity.

The growth factors that are released by the cells during exposure to low sodium medium were identified. Stimulation of cell multiplication was used as an assay for isolation of the growth-promoting activity. BSC-1 cells were exposed to low-sodium medium for 5 minutes and the conditioned medium was collected and filtered. Ultrafiltration and dialysis across membranes with specified molecular weight cut-offs indicated that the growth-promoting factor(s) has an apparent molecular weight of more than 3500 and less than 10,000. Gel-filtration chromatography on a Bio-Gel P-10 column revealed two factors with apparent molecular weights of 6200 and 9000.

The low sodium growth factors were resistant to treatment with dithiothreitol, which differentiated them from epidermal growth factor (EGF), transforming growth factor type alpha (TGF-alpha), insulin, and insulin-like growth factors that were inactivated by this reducing reagent. In addition, the low-sodium autocrine factor with a molecular weight of 6200 (AF-6.2) appeared distinct from known polypeptide mitogens for BSC-1 cells because 50 microliters of AF-6.2 in the presence of a maximal amount of either EGF (50 ng/milliliter), TGF-alpha (25 ng/milliliter), or insulin (5 micrograms/milliliter) exerted an additive effect on cell multiplication. Thus, AF-6.2 appears to differ chemically and physiologically from other known BSC-1 cell mitogens of similar size. Furthermore, the presence of AF-6.2 did not permit BSC-1 cells to grow in soft agar.

BSC-1 cells secrete a growth inhibitor protein (molecular weight, 24,000) that is similar in size and function to TGF-beta. Addition of the growth inhibitor (6 ng/milliliter) neutralized the growth-stimulating effect of the low-sodium growth factors. Thus, it appears that positive and negative autocrine growth factors act as determinants of proliferation of renal epithelial cells in culture.

The growth-promoting activity in the conditioned media indicated that it was resistant to freezing for several weeks and to heating to 56° C. for 30 minutes but it was destroyed at 100° C for 15 minutes. Activity was stable in 1% acetic acid and in the pH range from 3.1 to 9.5, but it was abolished by exposure to 0.1% trifluororacetic acid for 1 hour. Treatment with trypsin (100 micrograms/milliliter for 3 hour at 37° C.) eliminated activity, but dithiothreitol (65 millimoles for 1 hour at 22° C.) did not. These observations suggested that the low sodium growth-promoting activity is one or more proteins that have no disulfide bridges accessible to dithiothreitol.

To determine whether new protein synthesis was required for activity to appear in low-sodium conditioned medium, cultures were preincubated with cycloheximide (50 micrograms/milliliter) for 1 hour. Medium containing cycloheximide was aspirated and replaced by fresh low-sodium or control medium, which was then conditioned by the cells for 5 minutes. [$^3$H]Leucine incorporation into acid-insoluble material in the cells was inhibited by 85% during the 5 minutes of conditioning. The appearance of growth-stimulating activity in low-sodium conditioned medium was not reduced by inhibition of protein synthesis.

Low sodium-induced growth-promoting activity showed cell-type specificity, as low-sodium medium did not stimulate the growth of fibroblasts. Release was also cell-type specific, because conditioned medium from fibroblasts exposed to low-sodium medium did not stimulate growth of the epithelial cells.

Stimulation of cell multiplication was used as an assay for isolation of the growth-promoting activity. BCS-1 cells were exposed to low-sodium medium for 5 minutes and the conditioned medium was collected and filtered as described above. Ultrafiltration and dialysis across membranes with specified molecular weight cutoffs indicated that the growth-promoting factor has an apparent molecular weight of more than 3500 and less than 10,000. Gel-filtration ohromatography on a Bio-Gel P-10 column revealed two factors with apparent molecular weights of 6200 and 9000, as shown in FIG. 4. When the relative amount of each factor was assessed by serial dilution, the potency of the protein with a molecular weight of 6200 was approximately 10-fold greater than the protein with a molecular weight of 9000. The smaller protein was subjected to HPLC anion exchange on a Mono Q column. Elution was carred out with a gradient of choline chloride (0.1–0.4 molar) in 10 millimoles sodium phosphate buffer. The growth-promoting factor was eluted at a choline concentration of approximately 0.27 molar, as shown in FIG. 5. The material in this peak was subjected to electrophoresis on a NaDodSO$_4$/polyacrylamide gel containing 15% acrylamide and 6 molar urea. Silver staining of the gel revealed a single band with a molecular weight of approximately 6200.

The foregoing description is for purposes of illustration, rather than limitation of the scope of protection accorded this invention. The latter is to be measured by the following claims, which should be interpreted as broadly as the invention permits.

The invention claimed is:

1. A method of producing autocrine growth factors from African green monkey epithelial cells comprising:

preparing a confluent in vitro culture of said epithelial cells in a high sodium growth medium;

preparing a sterile low sodium medium for growing said epithelial cells wherein said low sodium medium has about 115 to 135 millimoles of sodium;

removing the high sodium medium from the confluent culture of cells;

contacting the confluent culture from which the high sodium growth medium has been removed with said low sodium medium for at least 4 minutes; and, recovering the autocrine growth factors with molecular weights of 6200 and 9000 Daltons as determined by SDS-polyacrylamide gel electrophoresis from said low sodium medium and said confluent culture of cells;

and wherein the autocrine growth factors:

(1) are resistant to treatment with 65 millimoles of dithiothreitol for one hour at 22° C., (2) are resistant to freezing for at least one week, (3) are resistant to heating at 56° C. for thirty minutes but are destroyed by treatment of 100° C. for fifteen minutes (4) are stable in 1% acetic acid and at a pH range from 3.1 to 9.5, and (5) where the cell proliferation activity of the autocrine factors is abolished by exposure to 0.1% trifluoroacetic acid for one hour or by treatment with 100 micrograms/milliliter of trypsin for three hours at 37° C.

2. The process of claim 1 wherein the high sodium growth medium contains glucose, sodium, biotin and calf serum, and said low sodium medium contains biotin and serum.

3. A process according to claim 1 wherein the growth medium contains glucose, sodium, biotin and calf serum, and said low sodium medium contains biotin, serum and has less than 135 millimolar sodium.

* * * * *